United States Patent [19]

Demus et al.

[11] Patent Number: 4,626,375
[45] Date of Patent: Dec. 2, 1986

[54] LIQUID CRYSTALLINE SUBSTANCES

[75] Inventors: Dietrich Demus; Roger Frach; Hans-Joachim Deutscher; Horst Zaschke, all of Halle, German Democratic Rep.

[73] Assignee: VEB Werk fuer Fernsehelektronik, Berlin-Oberschoeneweide, German Democratic Rep.

[21] Appl. No.: 659,388

[22] Filed: Oct. 10, 1984

[30] Foreign Application Priority Data

Oct. 28, 1983 [DD] German Democratic Rep. ... 256067

[51] Int. Cl.⁴ ............... C09K 3/34; G02F 1/13; C07C 69/76; C07C 69/74; C07C 121/00
[52] U.S. Cl. .................. 252/299.63; 252/299.5; 350/350 R; 350/350 S; 428/1; 562/491; 562/500; 560/57; 560/72; 560/101; 560/116; 560/118; 558/416
[58] Field of Search ............ 562/491, 500; 560/101, 560/116, 118, 57, 72; 252/299.63, 299.5; 350/350 R, 350 S; 260/465 D; 428/1

[56] References Cited

U.S. PATENT DOCUMENTS

| | | | |
|---|---|---|---|
| 3,764,621 | 10/1973 | Knowles | 562/491 |
| 4,001,137 | 1/1977 | Steinstrasser | 252/299.67 |
| 4,035,056 | 7/1977 | Coates et al. | 252/299.66 |
| 4,229,315 | 10/1980 | Krause et al. | 252/299.63 |
| 4,293,434 | 10/1981 | Deutscher et al. | 252/299.63 |
| 4,361,494 | 11/1982 | Osman et al. | 252/299.63 |
| 4,410,445 | 10/1983 | Baur et al. | 252/299.63 |
| 4,439,015 | 3/1984 | Rich et al. | 252/299.63 |
| 4,490,278 | 12/1984 | Schubert et al. | 252/299.63 |

FOREIGN PATENT DOCUMENTS

| | | | |
|---|---|---|---|
| 56501 | 7/1982 | European Pat. Off. | 252/299.61 |
| 2939782 | 4/1981 | Fed. Rep. of Germany | 252/299.64 |
| 3325727 | 1/1985 | Fed. Rep. of Germany | 252/299.61 |

OTHER PUBLICATIONS

Destrade, C., et al., Mol. Cryst. Liq. Cryst., vol. 59, pp. 273–288 (1980).

Primary Examiner—Teddy S. Gron
Attorney, Agent, or Firm—Jordan and Hamburg

[57] ABSTRACT

New liquid-crystalline esters of the 4-[(4-alkyl-cyclohexyl)-methyl]-benzoic acids or cyclohexanecarboxylic acids which are suitable for electro-optical displays have the general formula

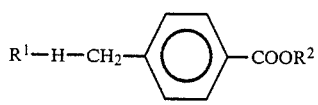

or -continued

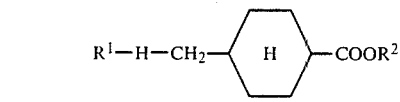

wherein
$R^1 = C_nH_{2n+1}$
$R^2 = H$,

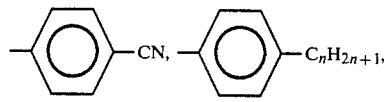

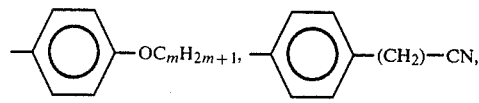

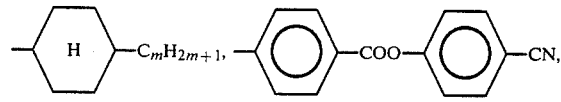

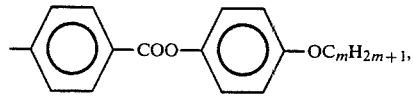

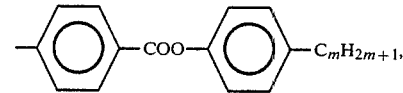

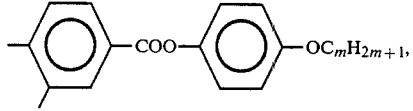

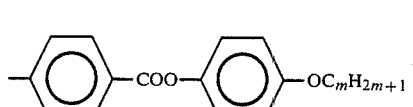

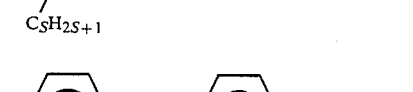

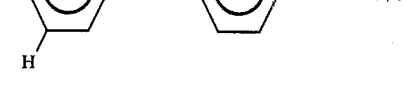

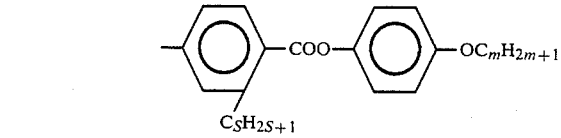

wherein (List continued on next page.)

n = an integer from 1 to 10,
m = an integer from 1 to 10,
S = an integer from 1 to 10.

The aforementioned esters are produced by converting the corresponding 4-alkylcyclohexanecarboxylic acid chloride according to Friedel-Crafts with benzene, reduction of the corresponding ketones to 4-alkyl-cyclohexyl-methyl-benzene, Friedel-Crafts acylation with acetyl chloride and oxidation with bromine to the 4-[(4-alkyl-cyclohexyl)-methyl]-benzoic acids, which are esterified according to conventional methods with substituted cyclohexanols or phenols or are hydrogenated with hydrogen and Raney-Nickel under high-pressure to 4-[(4-alkyl-cyclohexyl)-methyl]-cyclohexanecarboxylic acids, and then are esterified according to conventional procedures with substituted cyclohexanols or phenols.

20 Claims, No Drawings

LIQUID CRYSTALLINE SUBSTANCES

BACKGROUND OF THE INVENTION AND PRIOR ART STATEMENT

The invention relates to liquid crystalline substances for use in electro-optical devices for the display of numbers, symbols and images as well as to a method for their synthesis.

Known are 4-(cyclohexyl-methyl)-cyclohexanecarboxylic acids obtained by catalytic hydrogenation of 4-benzylbenzoic acid, see B. Willstätter, E. Waldschmidt-Leitz, Ber. dtsch. chem. Ges. 54, 1423 (1921); U.S. Pat. Nos. 3,679,805 (1972); 3,686,415 (1972); 3,689,566 (1972); 3,764,621 (1973).

New liquid crystalline compounds are the object of the invention.

BRIEF DESCRIPTION OF THE INVENTION

It has been found that new esters of the 4-[(4'-alkylcyclohexyl)-methyl]-benzoic acids or -cyclohexanecarboxylic acids having the general formula

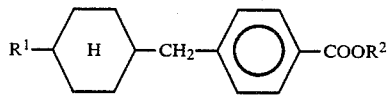

or

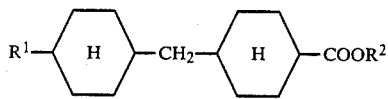

are suitable, wherein
$R^1 = C_nH_{2n+1}$
$R^2 = H$,

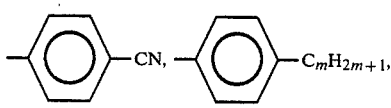

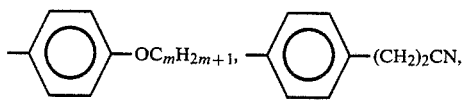

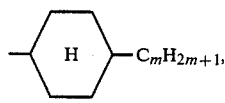

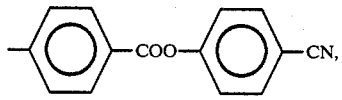

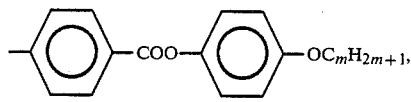

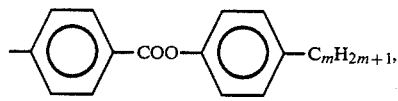

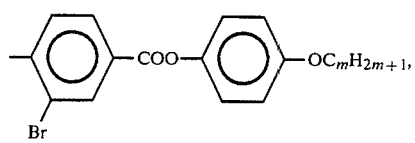

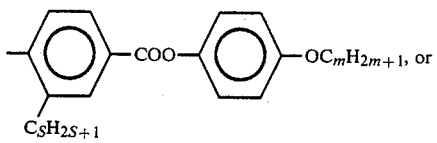

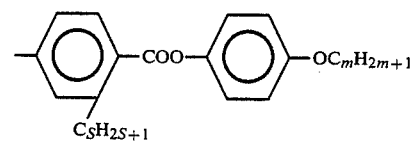

$S$ = an integer from 1 to 10 with
$n$ = an integer from 1 to 10, and
$m$ = an integer from 1 to 10.

It has been found that these new esters of the 4-[(4'-alkyl-cyclohexyl)-methyl]-benzoic acids or -cyclohexanecarboxylic acids have liquid crystalline properties.

Since methylene-bridge-bonded six-membered ring systems have an angular structure, it was surprising that the compounds according to the invention are liquid crystalline. D. Demm, D. Demus, H. Zaschke: *Flüssige Kristalle in Tabellen*, VEB Deutscher Verlag fuer Grundstoffindustrie Leipzig 1974; C. Destrade, Nguyen Huu Tinh, H. Gasparoux: Mol. Cryst. Liq. Cryst. 59, 273 (1980).

The substances have partially very low melting enthalpies $\Delta H$ and small values of optical double refraction $\Delta n$.

The esters are produced by converting the corresponding 4-alkylcyclohexanecarboxylic acid chloride according to Friedel-Crafts with benzene, reduction of the corresponding ketones I to 4-alkyl-cyclohexyl-methyl-benzene II, Friedel-Crafts acylation with acetyl chloride and oxidation with bromine to the 4-[(4'-alkylcyclohexyl)-methyl]-benzoic acids IV, which are esterified according to conventional methods with substituted cyclohexanols or phenols or are hydrogenated with hydrogen and Raney-Nickel under high-pressure to 4-[(4'-alkylcyclohexyl)-methyl]-cyclohexanecarboxylic acids V, and then are esterified according to conventional procedures with substituted cyclohexanols or phenols.

The synthesis occurs according to the following schematic representation:

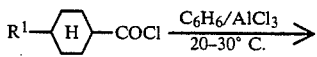

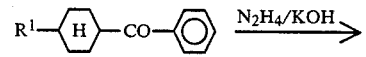

I

II

-continued

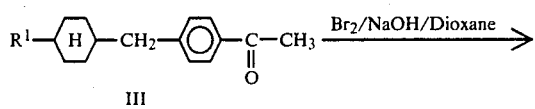
III

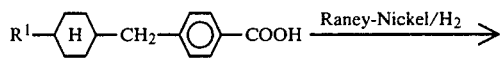
IV

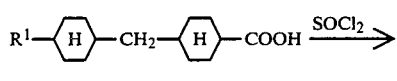
V

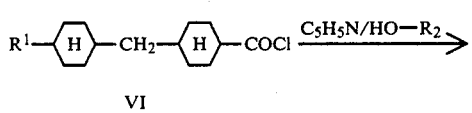
VI

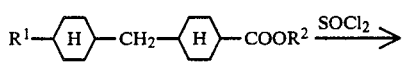
VII

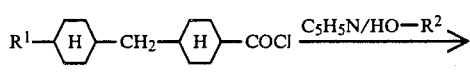
VIII

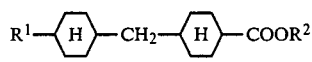
IX $R^1$ = alkyl
$R^2$ = hydrogen, aliphatic and carbocyclic alcohols, substituted phenols.

DETAILED DESCRIPTION OF PREFERRED EMBODIMENTS OF THE INVENTION

The invention will be further explained by means of the following four examples:

EXAMPLE 1

Table 1 gives examples of the esters of the 4-[(4'-alkylcyclohexyl)-methyl]-benzoic acids wherein
K = crystalline-solid
$S_1$, $S_2$ = smectic phases
N = nematic phase
is = isotropic-liquid

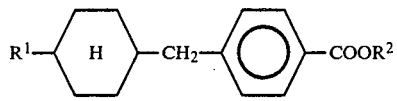

TABLE 1

| No. | $R^1$ | $R^2$ | K | N | is |
|-----|-------|-------|------|--------|----|
| 1/1 | $C_2H_5$ | 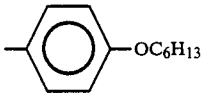 | .115 | .174.5 | . |
| 1/2 | $C_2H_5$ | 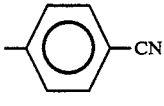 | .87 | (.84) | . |

EXAMPLE 2

Table 2 gives examples of the esters of the 4-[(4'-alkylcyclohexyl)-methyl]-cyclohexanecarboxylic acids of the general formula:

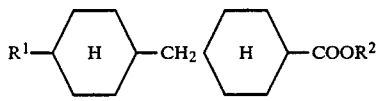

TABLE 2

| | $R^1$ | $R^2$ | K | $S_1$ | $S_2$ | N | is |
|---|---|---|---|---|---|---|---|
| 2/1 | $C_4H_9$— | —H | .107 | — | — | (.105) | . |
| 2/2 | $C_2H_5$ | 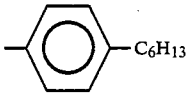—$OC_6H_{13}$ | .73 | (.57.5 | .60) | .83.5 | . |
| 2/3 | $C_2H_5$— | 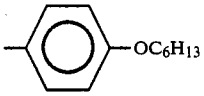—CN | .97 | — | — | (.95) | . |
| 2/4 | $C_4H_9$— | 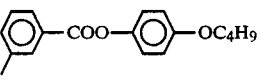—$C_6H_{13}$ | .51 | — | .70 | — | . |
| 2/5 | $C_4H_9$— | 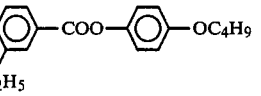—$OC_6H_{13}$ | .57 | — | .82 | .95 | . |

TABLE 2-continued

| | R¹ | R² | K | S₁ | S₂ | N | is |
|---|---|---|---|---|---|---|---|
| 2/6 | C₄H₉— | –⟨phenyl⟩–CN | .110 | — | — | (.108) | . |
| 2/7 | C₄H₉— | –⟨phenyl⟩–(CH₂)₂CN | .114.5 | — | (.90) | — | . |
| 2/8 | C₂H₅— | –⟨cyclohexyl, H⟩–C₅H₁₁ | .50 | — | .96 | — | . |
| 2/9 | C₄H₉— | –⟨cyclohexyl, H⟩–C₆H₁₃ | .25 | — | .118 | — | . |
| 2/10 | C₂H₅— | –⟨phenyl⟩–COO–⟨phenyl⟩–OC₄H₉ | .95 | — | .115 | .216,5 | . |
| 2/11 | C₂H₅— | –⟨phenyl⟩–COO–⟨phenyl⟩–CN | .92 | — | .151 | .267 | . |
| 2/12 | C₄H₉— | –⟨phenyl⟩–COO–⟨phenyl⟩–CN | .88 | — | .164 | .243 | . |
| 2/13 | C₄H₉— | –⟨phenyl⟩–COO–⟨phenyl⟩–OC₄H₉ | .85 | — | .124.5 | .189 | . |
| 2/14 | C₂H₅— | –⟨phenyl, Br⟩–COO–⟨phenyl⟩–OC₄H₉ | .82.5 | — | — | .178 | . |
| 2/15 | C₄H₉— | –⟨phenyl, Br⟩–COO–⟨phenyl⟩–OC₄H₉ | .79 | — | — | .175.5 | . |
| 2/16 | C₂H₅— | –⟨phenyl, C₂H₅⟩–COO–⟨phenyl⟩–OC₄H₉ | .52.5 | — | — | .131 | . |
| 2/17 | C₂H₅— | –⟨phenyl, CH₃⟩–COO–⟨phenyl⟩–OC₄H₉ | .63 | — | — | .157.5 | . |

TABLE 2-continued

| | R¹ | R² | | K | S₁ | S₂ | N | is |
|---|---|---|---|---|---|---|---|---|
| 2/18 | C₄H₉— | 4-methylphenyl-COO-4-butoxyphenyl (with CH₃ on first ring) | | .68 | — | — | .164.5 | . |
| 2/19 | C₄H₉— | phenyl-COO-4-hexylphenyl | | .40 | .157 | .174 | .185.5 | . |

EXAMPLE 3

1-benzoyl-4-n-butyl-cyclohexane (Ib)

To a stirred mixture of 500 ml abs. benzene and 240 g (1.8 mol) AlCl₃ at 20° C., within 60 minutes, are added, dropwise, 302 g (1.5 mol) of 4-n-butyl-cyclohexanecarboxylic acid chloride (cis-trans mixture). The clear orange-yellow solution is then heated to 40° C. for 1 to 2 hours, cooled and poured onto 500 ml ice/concentrated HCl. The organic phase is separated, washed with water, with 10% aqueous potassium hydroxide solution and washed with water again. The aqueous phase is extracted two to three times with benzene or ether. The combined organic extracts are dried over Na₂SO₄ and the solvent is removed in vacuum.

Thereby are obtained 315 g (86% of the theoretical amount) ketone which is sufficiently pure for further conversions. A specimen was recrystallized from n-hexane. F.P.: 56° to 59° C. (cis-trans mixture)

1-benzyl-4-n-butyl-cyclohexane (IIb)

315 g (1.3 mol) of non-purified 1-benzoyl-4-n-butyl-cyclohexane, 164 g (4 mol) of 78% hydrazine hydrate, 280 g (5 mol) of solid KOH and 1.5 l triethylene glycol are subjected to the usual conditions of a Wolff-Kishner reduction of the Huang-Minlong variant.

After the distillation of the raw product in vacuum are obtained 234 g (78% of the theoretical amount) 1-benzyl-4-n-butyl-cyclohexane.

B.P.: 114° to 116° C./0.3 mm (cis-trans mixture)

4-[(4'-n-butyl-cyclohexyl)-methyl]-benzoic acid (IVb)

To a stirred mixture of 200 ml abs. methylene chloride and 80 g (0.6 mol) AlCl₃ a solution of 92 g (0.4 mol) 1-benzyl-4-n-butyl-cyclohexane and 39 g (0.5 mol) acetyl chloride in 50 ml methylene chloride are added, dropwise, so that the temperature is maintained between 0° C. and 5° C. After that, it is stirred for 2 hours at room temperature, and then it is poured onto 200 ml ice/concentrated HCl. After separation, washing and drying of the organic phase, as well as removing the solvent in vacuum, a solid ketone is obtained, that is immediately subjected to a haloform reaction.

For this purpose, the ketone is dissolved in 300 ml dioxane and added dropwise, with stirring, to a hypobromide solution, which has been produced in the usual way from 336 g (6 mol) KOH in 1.2 l water and 288 g (1.8 mol) bromine. The temperature is thereby maintained at 5° to 10° C. After that, the solution is heated to 35° C., stirred again until the exothermic reaction declines, and maintained overnight. Then it is decanted from carbon tetrabromide and residues of bromoform or carbon tetrabromide are removed by means of steam distillation. The remaining aqueous solution is saturated with SO₂ and the benzoic acid is precipitated by pouring into half-concentrated H₂SO₄. The raw product is carefully washed and twice recrystallized from methanol.

Yield: 61 g (58% of the theoretical amount)

A specimen which has been recrystallized several times from benzene (60° to 85° C.) has a melting point F.P: 174° to 175° C. (cis-trans mixture)

EXAMPLE 4

4-[(4'-n-butyl-cyclohexyl)-methyl]-cyclohexanecarboxylic acid (2/1)

27.5 g (0.1 mol) 4-[(4'-n-butyl-cyclohexyl)-methyl]-benzoic acid were hydrogenated in 150 ml 15% aqueous KOH and Raney-Ni-(prepared from 40 g alloy) at 230° to 260° C. and 13 to 14 MPa in a high-pressure vibrating autoclave for 3 to 6 days.

Subsequently, the catalyst was filtered off and the filtrate was acidified with concentrated HCl. It is absorbed with ether, washed and dried over Na₂SO₄. After removal of the ether in vacuum are obtained 24 g (86% of the theoretical amount) acid (cis-trans mixture).

The absence of aromatic components can be confirmed by means of I.R.-, ¹H-NMR- or U.V. spectroscopy.

By repeated recrystallization from benzene (60° to 85° C.) a pure isomer is obtained that melts at 107° C. and is monotropically nematic starting at 105° C.

[-[(4'-n-butyl-cyclohexyl)-methyl]-cyclohexanecarboxylic acid chloride (Vib)

18 g (0.065 mol) acid are mixed at room temperature with 38 g (0.325 mol) thionyl chloride, maintained overnight and then boiled under reflux for 8 hours. Residual thionyl chloride is removed in water stream vacuum and the acid chloride is fractionally distilled.

Yield: 15 g (77.3% of the theoretical amount)
B.P.: 205° to 210° C./2 mm (cis-trans mixture)

4-[(4'-n-butyl-cyclohexyl)-methyl]-cyclohexanecarboxylic acid ester (VII)

To a solution of 0.006 mol of the substituted phenol or cyclohexanol in 15 ml pyridine are added, dropwise, 1.9 g (0.006 mol) 4-[(4'-n-butyl-cyclohexyl)-methyl]-cyclohexanecarboxylic acid chloride. The prepared mixture is maintained for one day at room temperature and/or heated from 70° to 80° C. for 3 or 4 hours. Then it is poured onto ice/concentrated HCl (100 g/20 ml), the ester is absorbed in ether, carefully washed with 1N NaOH solution, diluted HCl and water, dried with Na$_2$SO$_4$ and the solvent is distilled off. In the case of the esters VIId-h, the oily or solid residue is recrystallized from ethanol several times, whereby a complete separation of the cis-trans isomeric esters takes place.

In the case of the esters VIIk,j recrystallization is performed from ethanol/glacial acetic acid (2:1). The column chromatographic purification of these esters with basic Al$_2$O$_3$ (20 to 30 g) by eluting with 500 ml ethanol/acetic ester (1:1) and subsequent recrystallization from acetic ester in most cases results in a more rapid production of pure isomers.

The yields of the trans-product amount to 30 to 50% of the theoretical amount.

4-[(4'-ethyl-cyclohexyl)-methyl]-benzoylchloride (VIIIa)

14.8 g (0.06 mol) acid are mixed with 36 g (0.3 mol) thionylchloride at room temperature, maintained overnight and then boiled under reflux for 8 hours. Residual thionyl chloride is removed in water stream vacuum and the acid chloride is fractionally distilled.

Yield: 12 g (80.7% of the theoretical amount)
B.P.: 180° to 183° C./2 mm (cis-trans mixture)

4-[(4'-ethyl-cyclohexyl)-methyl]-benzoate (IX a,b)

To a solution of 0.006 mol of the substituted phenol in 15 ml pyridine are added, dropwise, 1.6 g (0.006 mol) [4-[(4'-ethyl-cyclohexyl)-methyl]-benzoyl chloride. The prepared mixture is maintained for one day at room temperature and heated to 70° to 80° C. for 3 to 4 hours. After cooling it is poured onto ice/concentrated HCl (100 g/20 ml), the ester is absorbed in ether, washed with 1N NaOH-solution, diluted HCl and water, dried over Na$_2$SO$_4$ and the solvent is distilled off. The solid residue is recrystallized from ethanol/acetic ester (2:1) whereby a complete separation of the cis-trans-isomeric esters takes place.

Yield of the trans-product: 40 to 60% of the theoretical amount

We claim:

1. Liquid-crystalline esters of 4-[(4'-alkyl-cyclohexyl)-methyl]-benzoic acids or -cyclohexanecarboxylic acids having the general formula

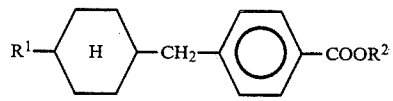

I or

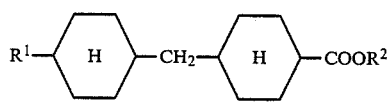

II wherein
R$^1$ in formulas I and II=C$_n$H$_{2n+1}$,
R$^2$ in formula I=

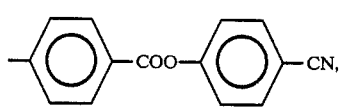

-continued

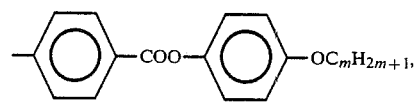

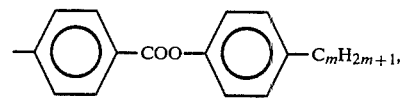

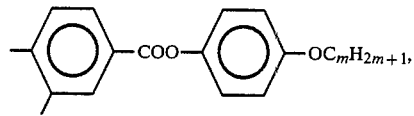

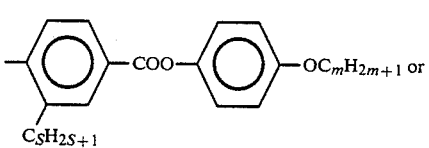

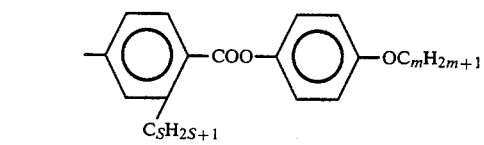

R$^2$ in formula II=

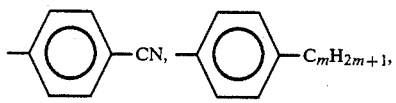

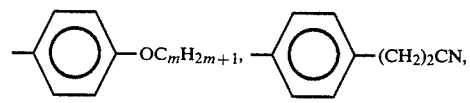

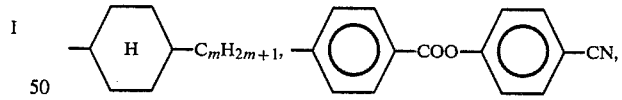

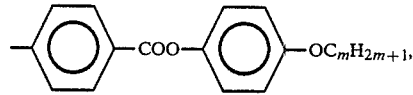

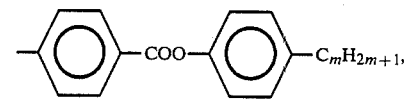

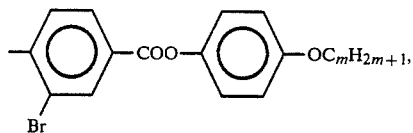

-continued

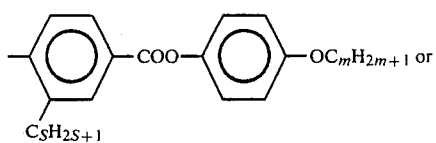

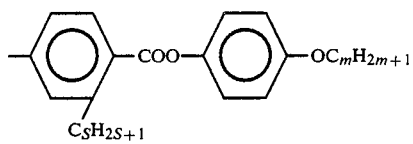

wherein in formulas I and II
n=an integer from 1 to 10
m=an integer from 1 to 10
S=an integer from 1 to 10.

2. A liquid-crystalline ester of the 4[(4'-alkyl-cyclohexyl)-methyl]-benzoic acids according to claim 1 wherein in the formula I $R^1 = C_2H_5$ and

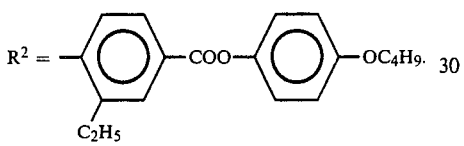

3. A liquid-crystalline ester of the 4-[(4'-alkyl-cyclohexyl)-methyl]-cyclohexanecarboxylic acids according to claim 1 wherein in the formula II $R^1 = C_2H_5$ and $R^2 =$ 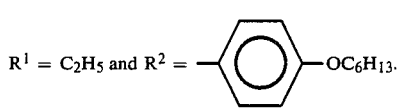

4. A liquid-crystalline ester of the 4-[(4'-alkyl-cyclohexyl)-methyl]-cyclohexanecarboxylic acids according to claim 1 wherein in the formula II $R^1 = C_2H_5$ and $R^2 =$ 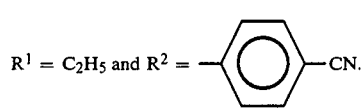

5. A liquid-crystalline ester of the 4-[(4'-alkyl-cyclohexyl)-methyl]-cyclohexanecarboxylic acids according to claim 1 wherein in the formula II $R^1 = C_4H_9$ and $R^2 =$ 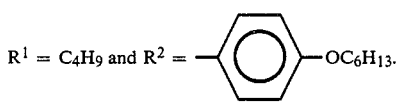

6. A liquid-crystalline ester of the 4-[(4'-alkyl-cyclohexyl)-methyl]-cyclohexanecarboxylic acids according to claim 1 wherein in the formula II $R^1 = C_4H_9$ and $R^2 =$ 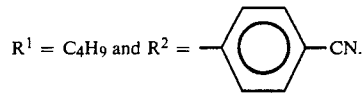

7. A liquid-crystalline ester of the 4-[(4'-alkyl-cyclohexyl)-methyl]-cyclohexanecarboxylic acids according to claim 1 wherein in the formula II $R^1 = C_4H_9$ and $R^2 =$ 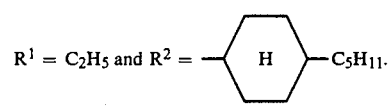

8. A liquid-crystalline ester of the 4-[(4'-alkyl-cyclohexyl)-methyl]-cyclohexanecarboxylic acids according to claim 1 wherein in the formula II $R^1 = C_2H_5$ and $R^2 =$ 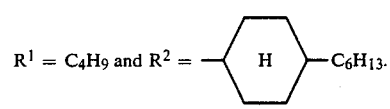

9. A liquid-crystalline ester of the 4-[(4'-alkyl-cyclohexyl)-methyl]-cyclohexanecarboxylic acids according to claim 1 wherein in the formula II $R^1 = C_4H_9$ and $R^2 =$ 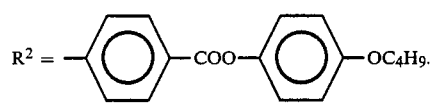

10. A liquid-crystalline ester of the 4-[(4'-alkyl-cyclohexyl)-methyl]-cyclohexanecarboxylic acids according to claim 1 wherein in the formula II $R^1 = C_2H_5$ and $R^2 =$ 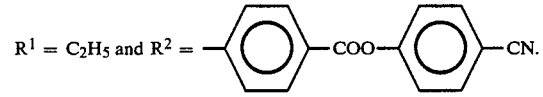

11. A liquid-crystalline ester of the 4-[(4'-alkyl-cyclohexyl)-methyl]-cyclohexanecarboxylic acids according to claim 1 wherein in the formula II $R^1 = C_2H_5$ and $R^2 =$ 12. A liquid-crystalline ester of the 4-[(4'-alkyl-cyclohexyl)-methyl]-cyclohexanecarboxylic acids according to claim 1 wherein in the formula II $R^1 = C_4H_9$ and $R^2 =$ 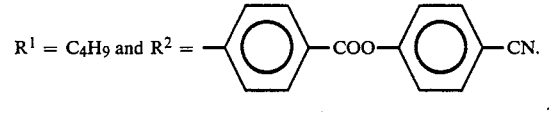

13. A liquid-crystalline ester of the 4-[(4'-alkyl-cyclohexyl)-methyl-cyclohexanecarboxylic acids according to claim 1 characterized by that in the formula II $R^1 = C_4H_9$ and

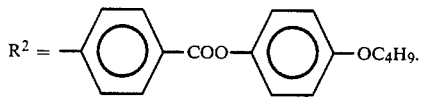

14. A liquid-crystalline ester of the 4-[(4'-alkyl-cyclohexyl)-methyl]-cyclohexanecarboxylic acids according to claim 1 wherein in the formula II $R^1 = C_2H_5$ and

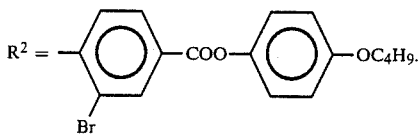

15. A liquid-crystalline ester of the 4-[(4'-alkyl-cyclohexyl)-methyl]-cyclohexanecarboxylic acids according to claim 1 wherein in the formula II $R^1 = C_4H_9$ and

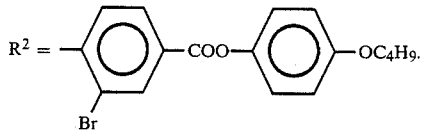

16. A liquid-crystalline ester of the 4-[(4'-alkyl-cyclohexyl)-methyl]-cyclohexanecarboxylic acids according to claim 1 wherein in the formula II $R^1 = C_2H_5$ and -continued

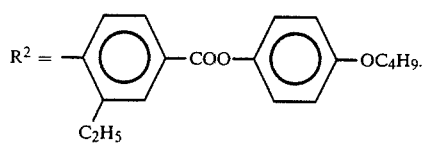

17. A liquid-crystalline ester of the 4-[(4'-alkyl-cyclohexyl)-methyl]-cyclohexanecarboxylic acids according to claim 1 wherein in the formula II $R^1 = C_2H_5$ and

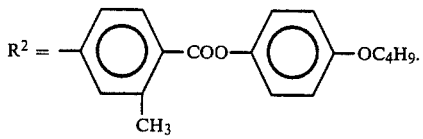

18. A liquid-crystalline ester of the 4-[(4'-alkyl-cyclohexyl)-methyl]-cyclohexanecarboxylic acids according to claim 1 wherein in the formula II $R^1 = C_4H_9$ and

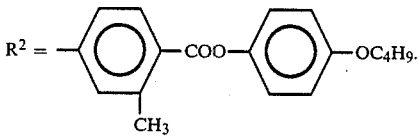

19. A liquid-crystalline ester of the 4-[(4'-alkyl-cyclohexyl)-methyl]-cyclohexanecarboxylic acids according to claim 1 wherein in the formula II $R^1 = C_4H_9$ and

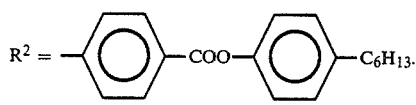

20. An electro-optical device for the display of numbers, symbols, and images, the device containing a liquid crystalline ester according to claim 1.

* * * * *